Figure 1:
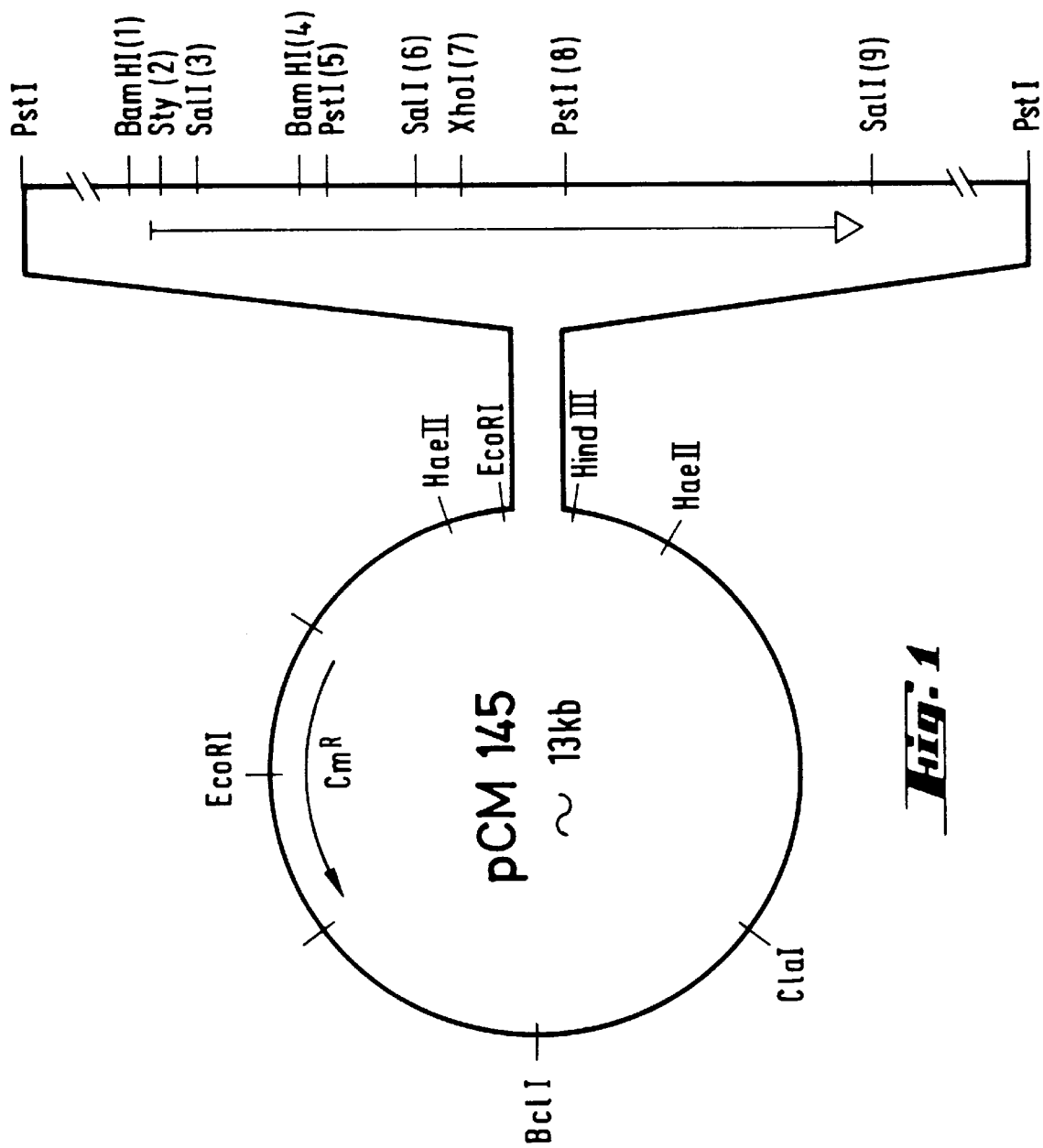

United States Patent [19]
Koller et al.

[11] Patent Number: 5,830,743
[45] Date of Patent: Nov. 3, 1998

[54] PROCESS FOR THE PREPARATION OF GLUTARYLACYLASE IN LARGE QUANTITIES

[75] Inventors: Klaus-Peter Koller, Bad Soden Am Taunus; Günther Johannes Riess, Frankfurt Am Main; Werner Aretz, Königstein/Taunus, all of Germany

[73] Assignee: Hoechst Aktiengesellschaft, Frankfurt am Main, Germany

[21] Appl. No.: 312,675

[22] Filed: Sep. 28, 1994

Related U.S. Application Data

[63] Continuation of Ser. No. 891,643, Mar. 16, 1992, abandoned.

[30] Foreign Application Priority Data

Mar. 18, 1991 [DE] Germany ............................. 41 08 823.9
Nov. 5, 1991 [DE] Germany ............................. 41 36 389.2

[51] Int. Cl.[6] .............................. C12N 9/78; C12N 15/63; C07H 21/04
[52] U.S. Cl. ........................ 435/227; 435/320.1; 536/23.2
[58] Field of Search .................. 435/43, 47, 48, 435/49, 50, 69.1, 227, 252.3, 252.33, 320.1; 436/22.1, 23.1, 23.2, 23.7

[56] References Cited

PUBLICATIONS

Matsuda et al., Journal of Bacteriology, 163:1222–1228 (1985).

Shibuya et al., Agricultural and Biological Chemistry, 45:1561–1567.

European Search Report dated Jul. 13, 1992.

Matsuda et al., "Molecular Cloning and Structure of the Gene for 7beta–(4–Carboxybutanamido)cephalosporanic Acid Acylase from a *Pseudomonas* Strain," Journal of Bacteriology, vol. 163, No. 3, pp. 1222–1228, Sep., 1985.

Skatrud et al., "Use of Recombinant DNA to Improve Production of Cephalosporin C by Cephalosporium Acremonium," Bio/Technology, vol. 7, pp. 477–485, 1989.

Glover, "Expression of Cloned DNAs in *E. coli* plasmids" from *Gene Cloning: The Mechanics of DNA Manipulation*, Chapman and Hall pp. 110–127, 1984.

Mizukami et al., Production of active human interferon–β in *E. coli*. 1. Preferential poduction by lower culture temperature. Biotechnol. Lett. vol. 8, No. 9, pp. 605–610, 1986, Abstract.

Georgiou, G. "Optimizing the production of recombinant proteins in microorganisms" AIChe Journal (Aug. 1988), vol. 34, No. 8, pp. 1233–1248.

Shibuya et al., "Isolation and Properties of 7β(4–Carboxybutanamido) cephalosporanic Acid Acylase . . . " *Agri. Biol. Chem* 45(7), pp. 1561–1567, 1981.

Schumacher et al, "Penicillin acylase from E. coli . . . " Nuc. Acids Res. 14(14), pp. 5713–5727, 1986.

Oh et al. "Complete nucleotide sequence of penicillin gacylase . . . " *Gene* 56, pp. 87–97, 1987.

Matsuda et al. "Molecular Cloning and Structure . . . " J. Bact. 163: p. 1222–1228, 1985.

Glover "Express of cloned DNAs in *E. coli* plasma" *Gene Cloning* p. 110–127, 1984.

Skudrud "Use of recombinant DNA to improve . . . " Biotechnology, vol. 7, pp. 477–485, May, 1989.

*Primary Examiner*—Robert A. Wax
*Assistant Examiner*—Kawai Lau
*Attorney, Agent, or Firm*—Finnegan, Henderson, Farabow, Garrett & Dunner, L.L.P.

[57] ABSTRACT

The gene encoding glutarylacylase (GA) contained in the plasmid pCM 145 (DSM 6409) permits the expression of GA in *E. coli* in high yields.

7 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CATGCTGAGA GTTCTGCACC GGGCGGCGTC CGC     33

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:2:

| Met | Leu | Arg | Val | Leu | His | Arg | Ala | Ala | Ser | Ala | Leu |
|---|---|---|---|---|---|---|---|---|---|---|---|
| -29 | | -25 | | | | -20 | | | | -18 | |

PROCESS FOR THE PREPARATION OF GLUTARYLACYLASE IN LARGE QUANTITIES

This application is a continuation of application Ser. No. 08/851,643 filed Mar. 5, 1992, now abandoned.

In the enzymatic preparation of 7-aminocephalosporanic acid from cephalosporin C there is initial formation of 7β-(4-carboxybutanamido)cephaloporanic acid (glutarylamidocephalosporanic acid), which is deacylated to 7-aminocephalosporanic acid with the aid of the enzyme glutarylacylase (or glutarylamidase), called "GA" hereinafter.

The genetic engineering preparation of GA in *E. coli* has already been described by R. Matsuda and K.-I. Komatsu, J. Bact. 163 (1985) 1222–1228. However, it was possible to increase the specific activity of GA only slightly (from 0.12 units of the strain employed to 0.2 units per mg).

Matsuda et al., loc. cit, use for their investigations a mutant Pseudomonas sp. GK 16, for which no depository number is indicated. The authors start from a strain Pseudomonas sp. SY-77-1 which is obtainable from the Fermentation Research Institute (FRI) under the number FERM 2410.

It has now been found that the GA-encoding gene can be isolated from a Pseudomonas strain, and that the enzyme can be obtained with the aid of this gene in *E. coli* with a specific activity which is at least five times higher. This enzyme isolated from the Pseudomonas strain is comparable with the GA from the deposited strain.

Preferred embodiments and further aspects of the invention are explained in detail hereinafter and defined in the patent claims.

It has emerged that cloning of the gene into a high copy number vector such as pUC18 leads under the normal induction conditions to killing of the transformed cells. For this reason low copy number vectors have been constructed for the following investigations and have been used to set up a gene bank of the strain. These vectors, plac10, plac100 and plac200, contain the origin of replication of the known plasmid pACYC 184 (A. C. Y. Chang and S. N. Cohen, J. Bact. 134 (1978) 1141–1156) and are therefore present in about five copies per cell. These vectors permit selection with chloramphenicol and thus avoidance of β-lactamase formation, which might act on cephalosporin.

For the identification of the GA gene, initially a gene bank which contained the complete genome digested with PstI was set up. 2 probes which correspond to codons 30 to 40 and 41 to 51 of the publication of Matsuda et al., loc. cit., were used to find a clone which contained a 3.7 kb PstI insert. The latter was partially sequenced after recloning into the phage M13mp19. This revealed a more than 98% agreement with the published sequence in the region of amino acids 51 to 209. The 3.7 kb PstI fragment was then radiolabelled and used as probe to screen a plasmid gene bank which had been constructed by cloning partially PstI-cut DNA of the strain into the low copy number vector plac 100. Restriction analysis and comparison of the cleavage sites with the published data revealed that the clone pCM 145 contains the complete gene for GA plus 5'- and 3'-flanking sequences. This clone contains the vector plac 100 with an approximately 10 kb PstI insert. It produces about 4 U/l GA. This clone was deposited on Mar. 8, 1991, under the provisions of the Budapest treaty at the Deutsche Sammlung von Mikroorganismen und Zellkulturen GmbH, Braunschweig, under deposit No. DSM 6409.

Figure 2:
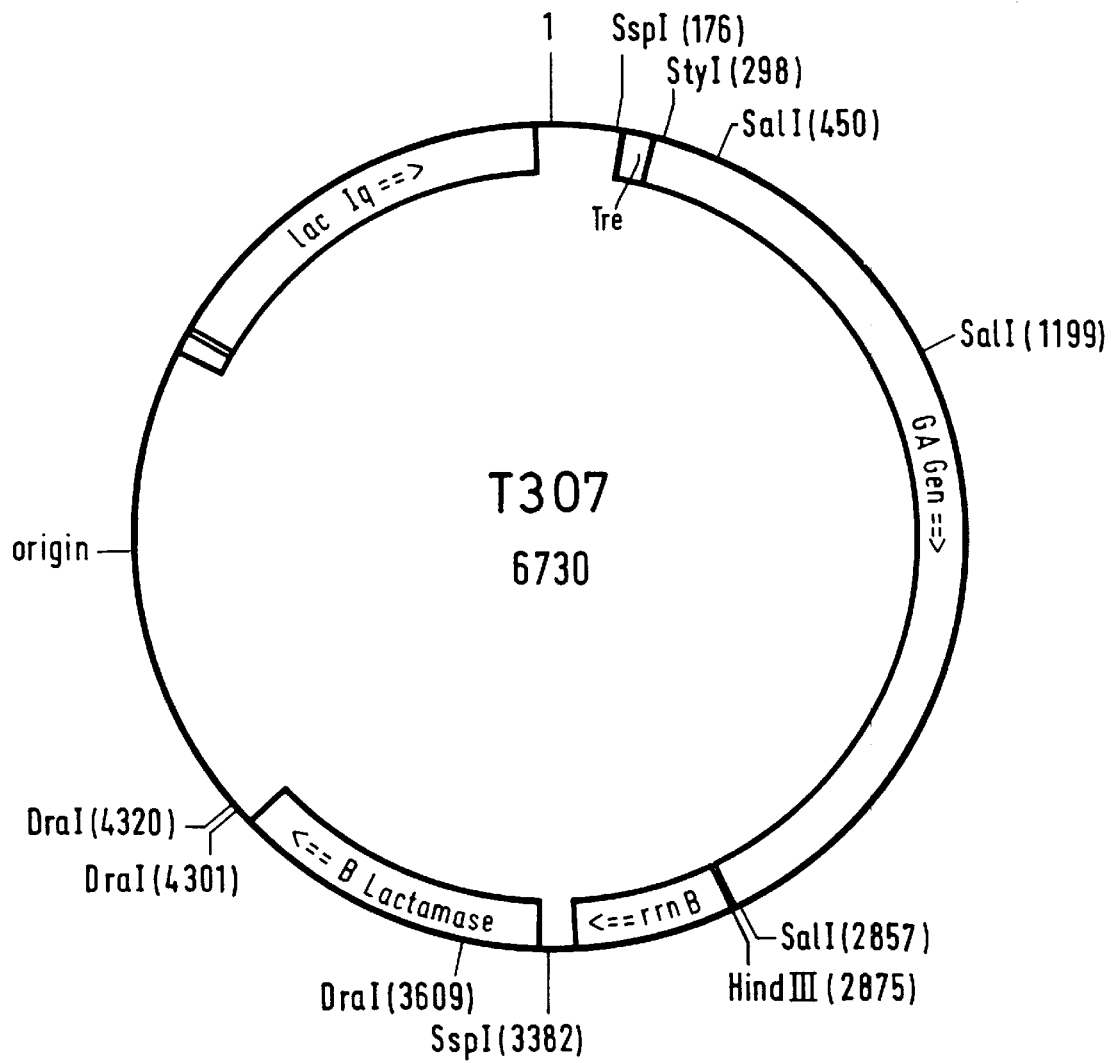
Figure 3:
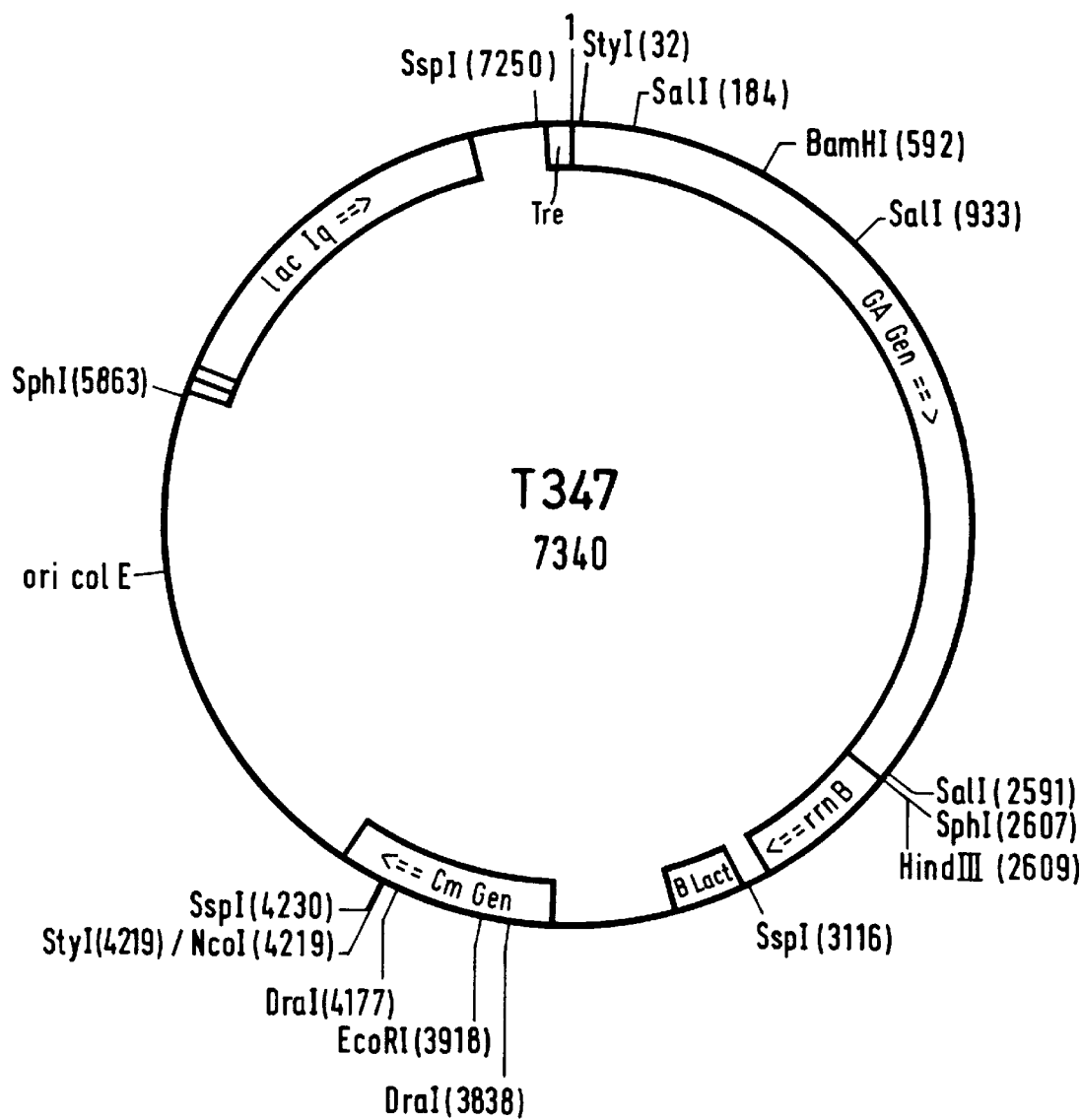
Figure 4:
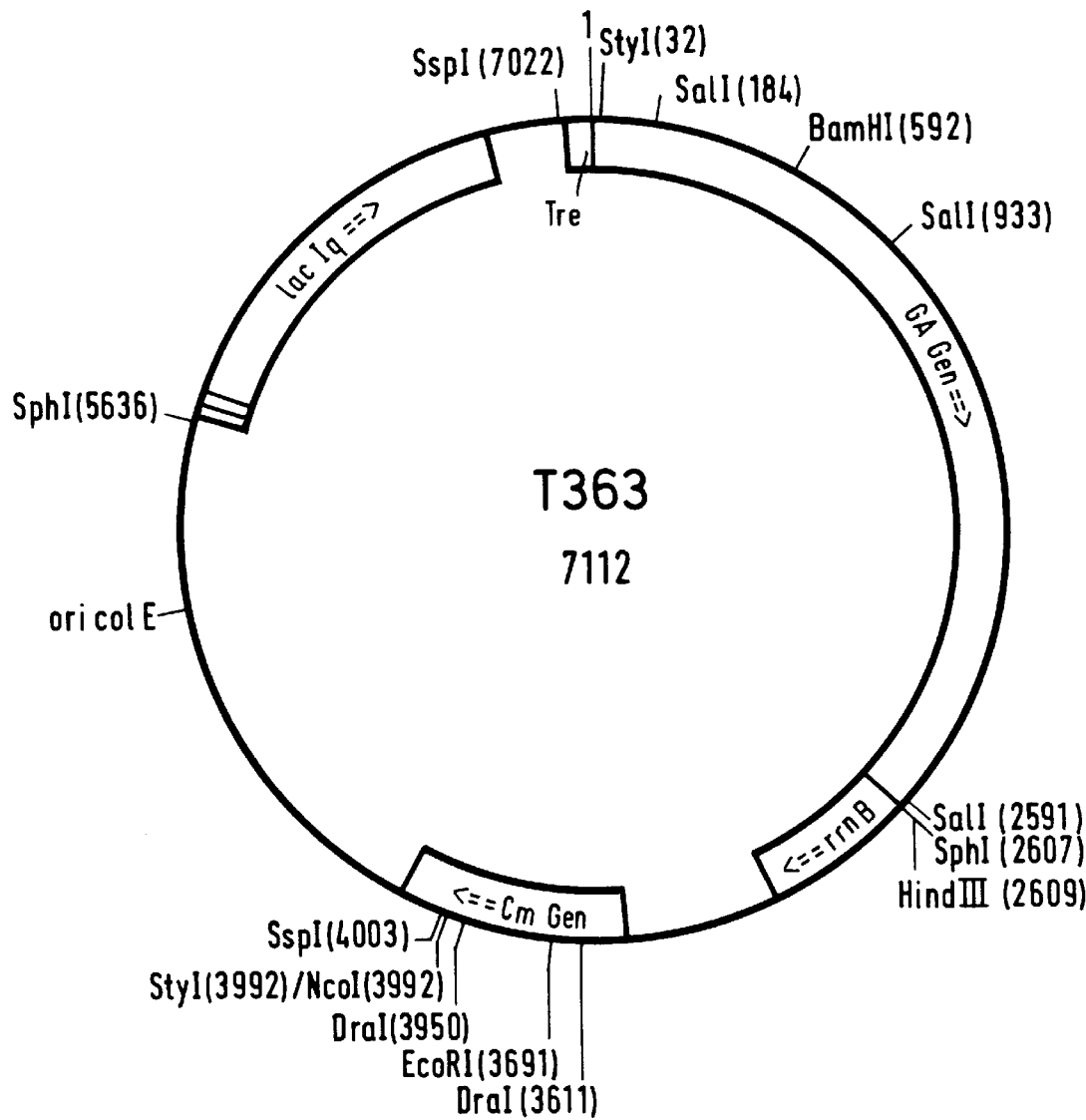

FIG. 1 shows a restriction map of the plasmid pCM 145. The restriction cleavage sites important for the clonings are numbered in the insert. FIG. 2 shows plasmid T307. FIG. 3 shows plasmid T347. FIG 4 shows plasmid T363.

It was possible further to increase the GA yields to about 450 U/l by recloning and subcloning.

Surprisingly, it emerged from this that reducing the fermentation temperature from 37° C. to 23° C., preferably 25°–30° C., in particular 27°–28° C., permits a distinct improvement in the yield. Fermentations at this temperature were possible for a lengthy period, whereas induction of the *E. coli* system with IPTG at 37° C. was lethal for the host strain.

Induction is preferably carried out in the logarithmic phase of growth, especially in the late logarithmic phase. The host strains preferably employed are *E. coli* K 12 strains which are free of or low in esterases, since working up is considerably facilitated in this way.

The productivity may be influenced by the host strain. Suitable strains proved to be, for example, *E. coli* MC 1061 (ATCC 53338), *E. coli* W 3110 (ATCC 27325) or *E. coli* DH1 (ATCC 33849).

It is possible to employ for the fermentation the known mineral media and complex media with yeast extract, peptone, tryptone or casamino acids. The most favorable conditions can be easily established by the person skilled in the art in simple preliminary tests.

The expression vector T 307 which was obtained by recloning and is described hereinafter (Example 4) gave a yield of about 1000 U/l of culture medium under induction conditions when the *E. coli* strain TG1 (supplied by Amersham-Buchler, Braunschweig) was used. The plasmid T 307 has a β-lactamase gene whose gene product, the enzyme β-lactamase, is used to select recombinant clones. β-Lactamase is, like GA, a secreted enzyme which is located in the periplasm. Surprisingly, it was then possible to show that replacement of parts of the β-lactamase structural gene by a chloramphenicol-resistance gene results in distinctly improved yields (compare Example 9, plasmid T 347). Resistance to chloramphenicol is mediated by the enzyme acetyltransferase (CAT) which, in contrast to β-lactamase, is located inside the cell.

It was possible to achieve a further improvement in the yield when not only parts of the β-lactamase structural gene are deleted but the complete structural gene region, especially the region encoding the signal peptide which is responsible for secretion of β-lactamase, is also deleted and the chloramphenicol acetyltransferase gene is likewise employed as selection marker (compare Example 10, plasmid T 363).

The invention accordingly also relates to the use of expression vectors which contain no gene for a secreted gene product or enzyme which is located in the periplasm as selection gene. It is then also possible to employ high copy vectors, preferably choosing vectors without a β-lactamase gene. It has been further found that optimal yields are achieved on use of the *E. coli* K 12 strains W 3110 M and MC 1061. In these cases moreover, these plasmids are not eliminated during the fermentation but are stable.

However, it is also possible in place of a selection marker which is active inside the cell to use a marker which is located in the periplasm or membrane if it is possible to reduce the expression of the marker during the production phase for the glutarylamidase to such an extent that it does not lead to instability of the plasmid. A suitable example is the tetracycline-resistance gene of Tu 1721, which is very strictly regulated (Klock, G. et al., J. Bacteriol. 161, 326–332, 1988) or comparably strictly regulated genes coding for markers located in the periplasm or membrane.

The constructions of the expression vectors necessary for achieving the high yields are described in detail hereinafter. The enzymes used were obtained from New England Biolabs (Schwalbach) or from Gibco/BRL (Eggenstein) and used in accordance with the manufacturers' instructions. Genetic engineering operations not described in detail were carried out in accordance with the detailed instructions in Ausubel et al., Current Protocols in Molecular Biology, Greene Publishing Associates and Wiley Interscience, 1987 and supplements.

All statements concerning the size of the plasmids (bp) are approximate statements.

Details of the invention are explained in the following examples. Unless stated otherwise, percentage data relate to weight.

EXAMPLES

1. Preparation of the plasmid plac10

The 1.1 kb EcoRI-HindIII fragment is isolated from the commercially available plasmid pBR 325 (SIGMA) and ligated to a 1.5 kb EcoRI-HindIII fragment from the vector pACYC 184. The mini-pACYC obtained in this way is partially digested with HaeII and ligated to the 819 bp HaeII fragment from the commercially available vector pUC12 which contains the polylinker and the α-complementation of lac Z. Vectors which contained the insert into the HaeII site from the pACYC 184 fragment in the arrangement such that the polylinker contained the cleavage sites in the sequence EcoRI-HindIII, followed by the origin of replication, were called plac10.

EXAMPLE 2

Preparation of the vectors plac100 and plac200

The mini-pACYC described in Example 1 contains 2 adjacent cleavage sites for ClaI at the HindIII cleavage site.

Deletion of this ClaI fragment from plac10 results in the vector plac100 which no longer contains the HindIII cleavage site used for the ligation to give mini-pACYC.

Partial digestion of plac100 with HaeII in analogy to Example 1, and replacement of the HaeII fragment with the polylinker from pUC 12 by the corresponding fragment from pUC 18 results in the vector plac200.

3. Setting up of a gene bank

The complete DNA of the Pseudomonas strain was totally digested with PstI and ligated into plac 10 cut with PstI. E. coli TG1 (pharmacia) was transformed with the ligation mixture.

Employed for the screening were initially 2 oligonucleotides which correspond to codons 30 to 40 and 41 to 50 of the published GA sequence. The clone pWK 96 which contains a 3.7 kb PstI insert was isolated in this way. The latter hybridized with both probes. Recloning into the phage M13mp19 and partial sequencing revealed more than 98% agreement with the published DNA sequence in the region of amino acids 150 to 209. Comparison with the published gene map shows agreement in the relevant cleavage sites.

The insert was radiolabelled and in turn used as probe for a gene bank set up from complete DNA partially digested with PstI, the clone pCM 145 which contains an approximately 10 kb insert being found. Restriction analysis and comparison with the published cleavage sites shows that the complete gene and the 5'- and 3'-flanking sequences were cloned. The clone provides a yield of 4 U/l GA. It is used as starting material for the following operations.

4. Reclonings

The plasmid plac 100 is cut with EcoRI and HindIII, and the insert with the GA gene is recloned into the commercially available vector pUC 19 which has been opened with the same enzymes. The clone T 286 obtained in this way provides a yield of 23.5 U/l GA. In this case part of the enzyme is secreted (in the starting strain the enzyme is found only in the periplasm).

To delete sequences which possibly hinder the expression of the gene in E. coli, the gene was reconstructed on the basis of the published map of the GA gene. In this connection reference is made to the numbering of the restriction cleavage sites in FIG. 1.

Firstly the BamHI fragment which is 0.8 kb in size (BamHI(1)–BamHI(4)) and which harbors a SalI cleavage site was cloned into the commercially available plasmid pUC 18. The resulting plasmid was cut with SalI and a SalI fragment which is likewise 0.8 kb in size (SalI(3)–SalI(6)) is inserted. The new plasmid was cut with PstI and a PstI fragment which is 0.9 kb in size (PstI(5)–PstI(8)) is cloned in, resulting in the clone pT 93. In addition, a 1.7 kb SalI fragment (SalI(6)–SalI(9)) was cloned into pUC 18 and examined for the correct orientation; the result is the plasmid pT 98. Since the cloned PstI fragment (PstI(5)–Pst(8)) contains an XhoI cleavage site, it was possible to clone the complete gene together by linking the EcoRI-XhoI fragment from pT 93 with the larger XhoI-EcoRI fragment, which also contains the origin of replication and the resistance gene, from pT 98. This results in the plasmid pT 103. E. coli cultures transformed therewith produce up to 130 U/l GA, the expression apparently being controlled by a 5'-promoter activity from the Pseudomonas DNA.

Isolation of the fragment with the GA gene from the plasmid pT103 after digestion with the restriction enzymes SstI and HindIII and cloning of it into the vector plac200 cut with the same enzymes results in the expression vector pT104 with which a GA yield of more than 1000 U/l is achieved.

Recloning of the reconstructed gene into the EcoRI-HindIII cleavage sites of the commercially available expression vector pBtac (manufactured by Boehringer-Mannheim) results in the plasmid pT 105. E. coli TG 1 strains transformed therewith produce after fermentation in shaken flasks at a fermentation temperature of 37° C. up to 288 U/l GA after 3 days.

A synthetic linker (SEQ ID NO: 1) is required for cloning the GA gene in the vector pTrc 99 A (E. Amann et al., Gene 69 (1988) 301–315):

```
    (NcoI)                                   (StyI)
 C  ATG CTG AGA GTT CTG CAC CGG GCG GCG TCC GC
    GAC TCT CAA GAC GTG GCC CGC CGC AGG CGG AAC
```

A BamHI(4)-StyI(2) fragment which is 0.57 kb in size is isolated from the plasmid pCM 145 after digestion with the enzymes StyI and BamHI (in the published DNA sequence the StyI cleavage site is located in the region of amino acids 11 to 13). This fragment and the abovementioned linker are ligated into the plasmid pTrc 99 A which has been cut with NcoI and BamHI, resulting in the plasmid T 297 with loss of the NcoI cleavage site.

Furthermore, a 1.5 kb SalI fragment (SalI(6)–SalI(9)) and a 0.34 kb BamHI-SalI fragment were isolated from the plasmid pCM 145 and ligated into the vector pUC 18 which has been opened with SalI and BamHI. This results in the plasmid T 306 which was examined for correct orientation of the SalI(6–9) fragment. A fragment 2.1 kb in size (which comprises the fragment from the BamHI(4) to the SalI(9) site) is isolated from the plasmid T 306 with the enzymes BamHI and HindIII. This fragment was ligated into the vector T 297 which had been opened with the enzymes BamHI and HindIII, resulting in the plasmid T 307 (FIG. 2). The *E. coli* population transformed therewith produces up to 260 U/l GA after fermentation at 28° C. for 2 days. Under modified fermentation conditions (see following examples) this yield can be increased to more than 780 U/l.

Induction of the system with IPTG at 37° C. is lethal for the transformed *E. coli* strain, which is apparently attributable to the use of the high copy number vector T 307. It is therefore carried out at temperatures below 30° C.

5. GA fermentation with *E. coli* clones

The *E. coli* clones DH1 T105 and TG1 T307 can be cultured on mineral and complex media and produce GA even in the logarithmic phase of growth. The maximal GA even in the achieved in the stationary phase. This shows that GA production depends on the growth rate. In both clones 50–60% of the enzyme is in the cytoplasm, 40–50% is in the periplasm and a maximum of 10% is in the culture filtrate.

For complete release of the GA the cells must be disrupted by ultrasound, a French press or a Dyno mill. The periplasm GA can be solubilized by detergents such as cetyltrimethylammonium chloride or toluene. Addition of EDTA and lysozyme increases the efficiency. Preliminary investigations on optimization of the fermentation parameters show that the clones are able to grow and produce in the temperature range from 25° C. to 37° C. However, at temperatures above 30° C. the partial pressure of oxygen must be kept <5%. A growth temperature of 28° C. results in an increase, which is required for GA production, in the doubling time to >2 h; under these conditions GA production is no longer dependent on a low $pO_2$. There has been found to be a distinct correlation between volume-based GA productivity (U/l of culture solution) and biomass concentration (g/l).

6. GA production in mineral medium

The clone TG1 T307 is maintained in YT-glycerol medium at −18° C.:

| | |
|---|---|
| Glycerol | 17.0% |
| Yeast extract | 0.7% |
| Bacto tryptone | 0.4% |
| NaCl | 0.4% |
| Ampicillin | 50 µg/ml |

Agar plates with the same medium are made up from this suspension and incubated at 28°–37° C. for 24 h, and the preculture is inoculated with a single colony.

| PC medium: | Bacto tryptone | 1% |
|---|---|---|
| | Yeast extract | 0.5% |
| | NaCl | 0.5% |
| | Ampicillin | 50 µg/ml |
| | pH = 7.2 | |

100ml of this nutrient solution in 300 ml Erlenmeyer flasks are incubated at 28° C. and 220 rpm for 24 h after inoculation. The culture then has an $OD_{578nm}$ of 3.0.

The following main culture (25 ml of nutrient solution/ 300 ml flask) is inoculated with 2% of the preculture and incubated at 28° C. and 220 rpm for 24–72 h:

| | % by weight |
|---|---|
| Mineral medium: | |
| $NaH_2PO_4$ | 1.110 |
| $Na_2HPO_4$ | 3.680 |
| KCl | 0.100 |
| $(NH_4)_2SO_4$ | 0.325 |
| $MgSO_4.7H_2O$ | 0.200 |
| Citric acid | 0.390 |
| Glycerol or glucose | 4.000 |
| $Fe_2(SO_4)_3.3H_2O$ | 0.0250 |
| Trace element solution | 0.1000 |
| pH | 6.0–6.5 |
| Trace element solution: | |
| $H_3BO_3$ | 0.208 |
| $(NH_4)_6Mo_7O_{24}$ | 0.080 |
| $ZnSO_4.7H_2O$ | 0.160 |
| $MnSO_4.4H_2O$ | 0.160 |
| $CuSO_4.5H_2O$ | 0.160 |
| KI | 0.048 |
| Biomass after 50 h: | 11 g/l |
| GA after 50 h: | 39 U/l |

7. GA production in complex medium

Strain maintenance and preculturing are carried out in analogy to Example 6, and a 5 l fermenter is inoculated with the following complex medium (31):

| Complex medium: | Bacto tryptone | 1% |
|---|---|---|
| | Yeast extract | 0.5% |
| | NaCl | 0.5% |
| | pH 7.2 | |
| Fermentation parameters: | 28° C., 400 rpm; 0.5 vvm | |
| Fermentation time: | 24–72 h | |
| Biomass after 72 h: | 7 g wet weight/l | |
| GA after 72 h: | 460 U/l of culture solution; | |
| | 66 U/g of wet weight | |

GA production in supplemented complex medium

The clone TG1 T307 was cultured in the following medium in analogy to Example 7:

| Complex medium: | Bacto tryptone | 2% |
|---|---|---|
| | Yeast extract | 1.0% |
| | NaCl | 0.5% |
| | pH 7.2 | |
| Fermentation parameters: | 28° C., 500 rpm; 0.8 vvm | |
| Biomass after 53 h: | 15 g of wet weight/l | |
| GA after 63 h: | 780 U/l of culture solution; | |
| | 52 U/g of wet weight | |

This example shows the relation between the increase in biomass and the increase in volume-based productivity.

Culturing of the strain DH1 T104 in analogy to Example 7 results in a biomass of 11 g of wet weight/l and a volume-based activity of 1040 U/l of culture solution with 97 U/g of wet weight after 70 hours. This corresponds to a specific activity of about 1 U/mg of protein.

8. Inducibility of GA production

Induction of the clone TG1 T307 in the late logarithmic phase of growth with IPTG (final concentration 1–5 mM) increases the yields by 60% in 5–10 hours.

EXAMPLE 9

Plasmid T 347

Isolated plasmid DNA from the strain TG1 (T 307) is completely cut with the enzyme DraI, and the larger fragment which contains the origin of replication and the GA gene under the control of the Trc promoter is isolated by electroelution from the 0.6% agarose gel used to separate the fragments.

A DNA fragment about 1.3 kb in size which contains the CAT gene and the regulatory region for the gene is liberated from the vector pACYC 184 (Chang and Cohen, J. Bacteriol. 134, 1141–1156, 1978) by digestion with the restriction enzyme Hae II. This fragment is likewise obtained by electroelution after separation in an agarose gel. The enzyme Hae II is used to produce at the ends of the fragment protruding 3' ends which are not suitable for ligation to the abovementioned Dra I vector fragment which contains blunt ends. The protruding ends of the Hae II fragment were therefore digested off with the exonuclease SI, and the fragment was subsequently treated with DNA polymerase I in the presence of the 4 deoxynucleotide triphosphates.

The Hae II fragment prepared in this way is ligated together with the Dra I vector fragment with the aid of the enzyme DNA ligase, and transformed into E. coli MC 1061. Suitable recombinant E. coli clones are selected for chloramphenicol resistance and synthesis of the enzyme GA. GA production was determined with the aid of the Schibuja assay. Recombinant clones contain the plasmid T 347 whose restriction map is depicted in FIG. 3. The orientation of the CAT gene in the vector is not crucial for the level of GA expression.

EXAMPLE 10

Plasmid T 363

It had emerged that when the fermentation time of E. coli MC 1061 (T 347) was prolonged the number of plasmid-harboring cells distinctly decreases after induction of GA expression by IPTG. The presumed reason for the instability is that a truncated β-lactamase protein which comprises about 69 amino acids and contains the signal peptide and the residues of β-lactamase is produced via the β-lactamase promoter which is still present. Since expression thereof cannot be prevented by cloning in the CAT gene, this probably leads to a negative selection pressure, i.e. loss of plasmid. In order to obtain a vector which was stable throughout the fermentation time, the plasmid T 307 was subjected to double digestion with the enzymes Ssp I and Dra I. The two largest fragments, which contain the origin of replication on the one hand, and the GA gene with its Trc promoter portion on the other hand, were isolated by electroelution after fractionation in a 0.6% agarose gel. The Hae II fragment with the CAT gene was prepared as in Example 9 and assembled together with the two abovementioned fragments with the aid of the enzyme DNA ligase. The ligation mixture was transformed into the E. coli strain MC 1061. Recombinant clones were selected on the basis of their ability to grow in the presence of chloramphenicol and to produce the enzyme GA.

Optimal yields were achieved with recombinant E. coli clones which harbor the plasmid T 363 whose restriction map is shown in FIG. 4.

EXAMPLE 11

Fermentation of the E. coli strains W 3110 (T 347) and W 3110 (T 363)

Culture conditions

All cultures were carried out, with the exception of the parameters to be varied, under the following conditions which were identical for both clones:

The clones are maintained in YT-glycerol medium at −18° C.:

| | | |
|---|---|---|
| Glycerol | 17.0% | |
| Yeast extract | 0.7% | |
| Bacto tryptone | 0.4% | |

-continued

| | | |
|---|---|---|
| NaCl | 0.4% | |
| Chloramphenicol | 25 µg/ml | |

Agar plates with the same medium are made up from this suspension and incubated at 28° C. for 24 hours, and the preculture (PC) is inoculated with a single colony.

| PC medium: | Bacto peptone | 0.1% |
|---|---|---|
| (NL 5295) | Yeast extract | 0.5% |
| | NaCl | 0.5% |
| | Chloramphenicol | 25 µg/ml |
| | pH = 7.2 | |

100 ml of this nutrient solution in 300 ml Erlenmeyer flasks are incubated at 28° C. and 220 rpm for 24 hours after inoculation. The culture then has an $OD_{578nm}$ of 6.0–8.0.

The following main culture (MC) is inoculated with 5–10% of this PC (based on PC with $OD_{578nm}$=3.0):

| MC: | NL 5292 + 1 ml Desmophen |  |
|---|---|---|
|  | 20.0 g/l yeast extract (Oxoid) |  |
|  | 1.2 g/l $NaH_2PO_4 \times H_2O$ |  |
|  | 8.5 g/l $Na_2HPO_4 \times 2H_2O$ |  |
|  | 1.0 g/l KCl |  |
|  | 2.0 g/l $MgSO_4 \times 7H_2O$ (autoclaved separately) |  |
|  | 0.25 g/l citric acid |  |
|  | 5.0 g/l $NH_4Cl$ |  |
|  | 4.0 ml/l SLA 5029 |  |
|  | 0.005 g/l thiamine → sterilized by filtration |  |
|  | (5 mg/10 ml → 0.5/50 ml Nl) |  |
|  | pH = 6.5 |  |
| Ferm. cond.: | Temp.: | 28° C. |
|  | Vol.: | 3.5 L |
|  | vvm: | 0.75 |
|  | rpm: | 500 (r = 7 cm) |
|  | pH: | 7.0 ± 0.2 (kept constant with 25% $NH_4OH$) |
| Fedbatch: | Glycerol solution: | 525 g of glycerol (99%)/L of MC medium (without yeast extract and $NH_4Cl$) |
|  | Feeding rate: | 3.4 ml/L*h with continuous addition (max. glycerol concentration in fermenter: 0.2%) or single addition |
|  | Start of feeding: | at $pO_2$ = 40–50% or $OD_{578\ nm}$ = 7–9 after a fermentation time of about 7 h |
|  | Duration of feeding: | 40–60 hours |
|  | $pO_2$: | kept constant at about 40% |
| Induction: | Induction with IPTG (1 mM final concentration) is carried out after a biomass of 70–80 g wet/L is reached after about 20 hours. The glycerol feeding should be continued for 4–40 hours thereafter. |  |
| Harvesting: | 24–48 hours after induction. |  |

GA expression in E. coli T 347

A fedbatch fermentation was developed with the clone T 347 with the aim of not only increasing the biomass but also demonstrating the inducibility of GA.

To do this, various feeding strategies for glycerol and the effects thereof on IPTG induction were investigated:

| Mode of glycerol addition | Wet biomass g/L | GA activity U/L | U/g |
|---|---|---|---|
| No feeding | 14 | 490 | 35 |
| 1% glycerol | 33 | 1219 | 37 |
| 1% glycerol + 1 mM IPTG | 41 | 2400 | 59 |
| Continuous glycerol (3.5%) + 1 mM IPTG | 61 | 3800* | 62 |

*40% GA intracellular

The above Table illustrates the good correlation of the increase in biomass and increase in GA and shows the enhancement of GA expression by IPTG, which is not repressed by ammonium but is repressed by glycerol and glucose in concentrations greater than 0.2%. 1 mM IPTG proved to be a sufficient concentration of inducer. The optimal induction time is when the culture changes to the stationary phase of growth.

Investigations of the plasmid stability of this construct revealed that at the time of induction (fermentation for about 40 hours) only 60% of the clones now contained the plasmid and that the plasmid is lost within 24 hours after addition of inducer. A plasmid half-life of <50 hours was determined in continuous culture.

GA expression in *E. coli* T 363

The clone T 363 has a plasmid which is still present in all cells after fermentation for 72 hours. The consequence of this is that distinctly higher GA titers are reached in the fermentation. Under the abovementioned optimal fedbatch conditions, up to 100 g wet weight with 7000–12,000 U of GA/L of culture liquid can be produced in about 70 hours. A maximum of 40% of this activity is located in the cytoplasm.

In order to elucidate which factors influence induction, the following parameters were investigated in more detail:

1) Fermentation temperature

The highest volume-based yields are achieved with maximum specific activity in the range 25°–28° C. At 37° C., the clone grows only to distinctly reduced biomasses and expresses only a maximum of 20 U of GA/L. A temperature shift from 37° C. to 28° C. at the time of induction likewise does not result in GA expression.

2) Complex nitrogen sources

It was possible to show that with regard to volume-based GA productivity the yeast extract from Oxoid can be replaced by that from Bio Springer or Marcor. Of the other complex nitrogen sources, the NZ amines A, B, E and L supplied by Sheffield, and lactalbumin, soypeptone and Bacto peptone, still provide 50–70% of the volume-based activity. With regard to specific GA activity, distinctly higher values are usually achieved with the NZ amines, lactalbumin and Bacto peptone.

Yeast extract (15–30 g/L) is the best complex nitrogen source to date.

3) Inducer concentration

Investigations in the range 1–10 mM IPTG revealed that 1 mM inducer suffices for best GA expression, but higher concentrations are not disadvantageous.

4) Oxygen supply

At the time of induction, *E. coli* T 363 has produced about 80% of its biomass, and the oxygen requirement is about 50 mmol/L*h. For this the $pO_2$ is kept at 40% saturation. The $pO_2$ plays only a small part in the induction itself as long as it remains above 10% of saturation.

EXAMPLE 12

Fermentation of *E. coli* K12 (GA)

| | |
|---|---|
| Strain: | *E. coli* K12 W3110M: Delta M 15 lac I$^q$ pT 363/33 |
| Strain maintenance: | Storage in ampoules (16.67% glycerol stock in 2 × LB medium) at −74° C. (deepfreeze) |
| 2 × LB medium: | Bacto tryptone (Difco) 20 g/l |
| | Bacto yeast extract (Difco) 10 g/l |
| | NaCl 5 g/l |
| Shake culture: | 1000 ml of 2 × LB medium (in 2 l steel flasks) containing 25 mg of chloramphenicol (added through sterilizing filter after sterilization of the medium) are inoculated with the contents of an ampoule and incubated at 28° C. on a shaker (250 rpm, amplitude 1.25 cm) for 4–5 h until the OD is 1.0. |
| Preliminary stage: | A DT fermenter (200 l effective volume) is 0.5% inoculated with a 1 l shake culture (OD 1.0). After growth for about 6 h, an OD of 3–4 is reached for transfer to the main stage. |

Preliminary stage medium:

| | |
|---|---|
| Yeast extract (Bio Springer) | 20.00 g/l |
| $Na_2HPO_4$ | 0.24 g/l |
| $NaH_2PO_4$ | 1.70 g/l |
| KCl | 0.20 g/l |
| $MgSO_4 * 7H_2O$ | 0.40 g/l |
| Citric acid | 0.05 g/l |
| $(NH_4)_2SO_4$ | 1.00 g/l |
| Thiamine/HCl | 1.00 mg/l |
| Trace element solution 5029 | 0.03 ml/l |
| Desmophen 3600 | 0.18 ml/l |

Trace element solution 5029:

| | |
|---|---|
| $CoCl_2 * 6H_2O$ | 2.00 g/l |
| $NiCl_2 * 2H_2O$ | 0.08 g/l |
| $CuCl_2 * 2H_2O$ | 0.08 g/l |
| $ZnCl_2$ | 0.80 g/l |
| $H_3BO_3$ | 4.00 g/l |
| $Na_2MoO_4 * 2H_2O$ | 2.40 g/l |
| $FeSO_4 * 7H_2O$ | 1.60 g/l |
| Adjust pH to 2.5 with HCl | |
| EDTA | 0.40 g/l |

The following conditions are maintained during the preliminary stage fermentation:
Temperature: 28° C.; pressure: 1.0 bar; air input: 7 m³(STP)/h; revolutions: (max. = 175 rpm); pH: 7.2 kept with $NH_3$ gas (before inoculation, the pH of the medium is raised from about 3.0–3.5 to 7.2).

| | | |
|---|---|---|
| Main stage: | An ET fermenter (2 m³ effective volume) is 10% inoculated with DT culture broth. The fermentation time is 60–80 hours. Main stage medium:. | |
| | Yeast extract (Bio Springer) | 20.00 g/l |
| | Na₂HPO₄ | 1.20 g/l |
| | NaH₂PO₄ | 8.50 g/l |
| | KCl | 1.00 g/l |
| | MgSO₄ * 7H₂O | 2.00 g/l |
| | Citric acid | 0.25 g/l |
| | (NH₄)₂SO₄ | 5.00 g/l |
| | Thiamine/HCl | 5.00 mg/l |
| | Trace element solution 5029 | 0.50 ml/l |
| | Desmophen 3600 | 0.30 ml/l |
| | The following fermentation conditions are set: | |
| Temperature: | 28° C. | |
| Pressure: | 1.0 bar | |
| Power input: | 2.5 kW/m³ | |
| Revolutions: | 120 rpm (with a diameter of 600 mm for the turbo stirrer); | |
| Air input: | 80 m³(STP)/h (0.67 vvm) | |
| pH: | 7.2 (controlled by subsequent addition of glucose) | |
| Induction: | with 1 mM IPTG at OD 50 | |
| Subsequent addition: | Glucose (30% strength solution); start after 6–8 h; amount: 0.5 g/l and h to 2.5 g/l and h (dependent on pH change). | |

In the initial phase of growth, the strain initially utilizes the yeast extract and, when metering in of glucose starts, grows exponentially further until the OD is 50. At the same time, the partial pressure of oxygen falls to 30 to 10%. For an adequate oxygen supply ($pO_2 \geq 30\%$) for the strain during exponential growth, the power input can be raised by increasing the revolutions and/or increasing the air input to 3.5 kW/m³ or more.

The pH is kept at 7.2 during this first fermentation phase by a stepwise or continuous increase in the metering in of glucose.

The second phase of the fermentation starts with induction of product formation by addition of 1 mM IPTG (isopropyl thiogalactoside) to the culture broth (OD 50 about 20–24 h).

In the subsequent course of the fermentation the product (glutarylamidase) is synthesized with an average production rate of 150–200 U/l and hour. During this the strain changes to linear growth. The subsequent metering in of glucose is reduced to about 0.5 g/l and h to keep the pH constant (7.2).

After running for 60–80 h, the fermentation can be stopped when the biomass has grown to 80–100 g/l wet weight (dry weight 22–25 g/l) and with formation of 7000–10,000 U/l product.

We claim:

1. A process for the preparation of glutarylacylase (GA) comprising:
   (a) recloning the GA gene contained in the plasmid pCM 145 (DSM 6409) without any 5'-regulatory sequences of said GA gene downstream of an inducible *E. coli* promoter, and
   (b) bringing about expression of said GA gene in *E. coli* at a fermentation temperature of 25°–30° C., wherein the induction takes place in the late logarithmic phase.

2. The process as claimed in claim 1, wherein the GA gene is recloned in a low copy number vector.

3. The process as claimed in claim 1, wherein the GA gene is present in an expression vector said expression vector containing no selection gene for a secreted enzyme that is located in the periplasm after expression.

4. The process as claimed in claim 3, wherein the expression vector is s high copy number vector.

5. The process as claimed in claim 1, wherein the GA gene is recloned in a high copy number vector comprising a strictly regulated selection gene.

6. The plasmid T 347.

7. The plasmid T 363.

* * * * *

UNITED STATES PATENT AND TRADEMARK OFFICE
CERTIFICATE OF CORRECTION

PATENT NO. : 5,830,743
DATED : November 3, 1998
INVENTOR(S) : Koller et al.

It is certified that error appears in the above-identified patent and that said Letters Patent is hereby corrected as shown below:

Title Page, Item [75], in the Inventors, lines 1 and 3, "Am" should read --am--.

Claim 3, col. 14, line 2, after "vector" (first occurrence), insert --,--.

Claim 4, col. 14, line 6, "is s" should read -- is a--.

Signed and Sealed this

Second Day of November, 1999

*Attest:*

Q. TODD DICKINSON

*Attesting Officer*　　　　*Acting Commissioner of Patents and Trademarks*